(12) United States Patent
Ciarrocca

(10) Patent No.: US 7,147,635 B2
(45) Date of Patent: Dec. 12, 2006

(54) BIPOLAR ELECTROSURGICAL SNARE

(75) Inventor: Scott Ciarrocca, Stockton, NJ (US)

(73) Assignee: Ethicon, Inc., Somerville, NJ (US)

( * ) Notice: Subject to any disclaimer, the term of this patent is extended or adjusted under 35 U.S.C. 154(b) by 169 days.

(21) Appl. No.: 10/767,093

(22) Filed: Jan. 29, 2004

(65) Prior Publication Data

US 2005/0171532 A1   Aug. 4, 2005

(51) Int. Cl.
*A61B 18/18*   (2006.01)

(52) U.S. Cl. .......................... 606/48; 606/45; 606/113

(58) Field of Classification Search ................. 606/41, 606/45–50, 113–114
See application file for complete search history.

(56) References Cited

U.S. PATENT DOCUMENTS

| | | | |
|---|---|---|---|
| 3,805,791 A | | 4/1974 | Seuberth et al. |
| 3,901,242 A | | 8/1975 | Storz |
| 3,910,279 A | * | 10/1975 | Okada et al. ................. 606/47 |
| 3,955,578 A | | 5/1976 | Chamness et al. |
| 4,202,338 A | | 5/1980 | Bitrolf |
| 4,311,143 A | | 1/1982 | Komiya |
| 4,345,599 A | | 8/1982 | McCarrell |
| 4,493,320 A | | 1/1985 | Treat |
| 4,905,691 A | | 3/1990 | Rydell |
| 5,078,716 A | | 1/1992 | Doll |
| 5,318,564 A | | 6/1994 | Eggers |
| 5,637,090 A | * | 6/1997 | McGee et al. ............ 604/95.01 |
| 5,697,281 A | | 12/1997 | Eggers et al. |
| 5,697,536 A | | 12/1997 | Eggers et al. |
| 5,697,882 A | | 12/1997 | Eggers et al. |
| 5,697,909 A | | 12/1997 | Eggers et al. |
| 5,730,127 A | * | 3/1998 | Avitall ......................... 600/374 |
| 5,863,291 A | * | 1/1999 | Schaer ........................ 606/41 |
| 6,050,995 A | | 4/2000 | Durgin |
| 6,071,274 A | * | 6/2000 | Thompson et al. .......... 604/528 |
| 6,106,522 A | * | 8/2000 | Fleischman et al. .......... 606/41 |
| 6,314,963 B1 | * | 11/2001 | Vaska et al. ................. 128/898 |
| 6,514,248 B1 | * | 2/2003 | Eggers et al. .................. 606/41 |
| 6,527,769 B1 | * | 3/2003 | Langberg et al. ............. 606/41 |
| 6,540,742 B1 | * | 4/2003 | Thomas et al. ................ 606/41 |
| 6,733,496 B1 | * | 5/2004 | Sharkey et al. ................ 606/41 |
| 2002/0188290 A1 | | 12/2002 | Sharkey et al. |
| 2003/0069574 A1 | | 4/2003 | Sliwa, Jr. et al. |

FOREIGN PATENT DOCUMENTS

| | | |
|---|---|---|
| EP | 0 916 360 A2 | 5/1999 |
| WO | WO 99/22799 A1 | 5/1999 |
| WO | WO 02/38052 A2 | 5/2002 |

* cited by examiner

OTHER PUBLICATIONS

European Search Report dated Mar. 31, 2005, for corresponding EP application 05250243.2.

*Primary Examiner*—Michael Peffley
*Assistant Examiner*—Alex Toy

(57) ABSTRACT

A bipolar electrosurgical instrument including an introducer having a channel therein and an electrically conductive snare slidably positioned within the channel and slidable between an undeployed position wherein it is substantially retracted within the channel and a deployed position wherein a distal portion of the snare extends outwardly from the channel. The electrically conductive snare is substantially insulated along its length but has an active and a return electrode exposed through a predetermined exposed section. The instrument further includes a retention element at a distal end of the snare for securing the distal end of the snare to the introducer to form a looped configuration of the snare, and at least one fluid delivery channel extending through the introducer between a fluid inlet sand a fluid outlet at the distal end of the introducer and located in proximity to the exposed section of the snare.

20 Claims, 12 Drawing Sheets

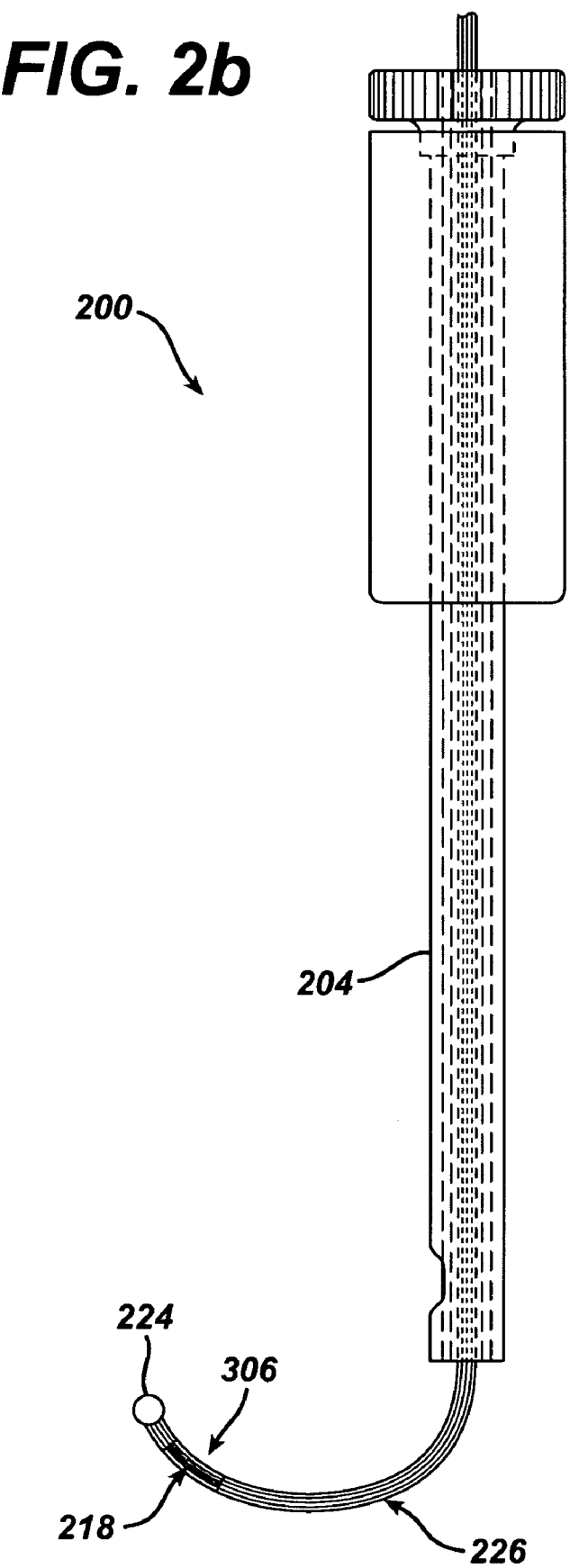

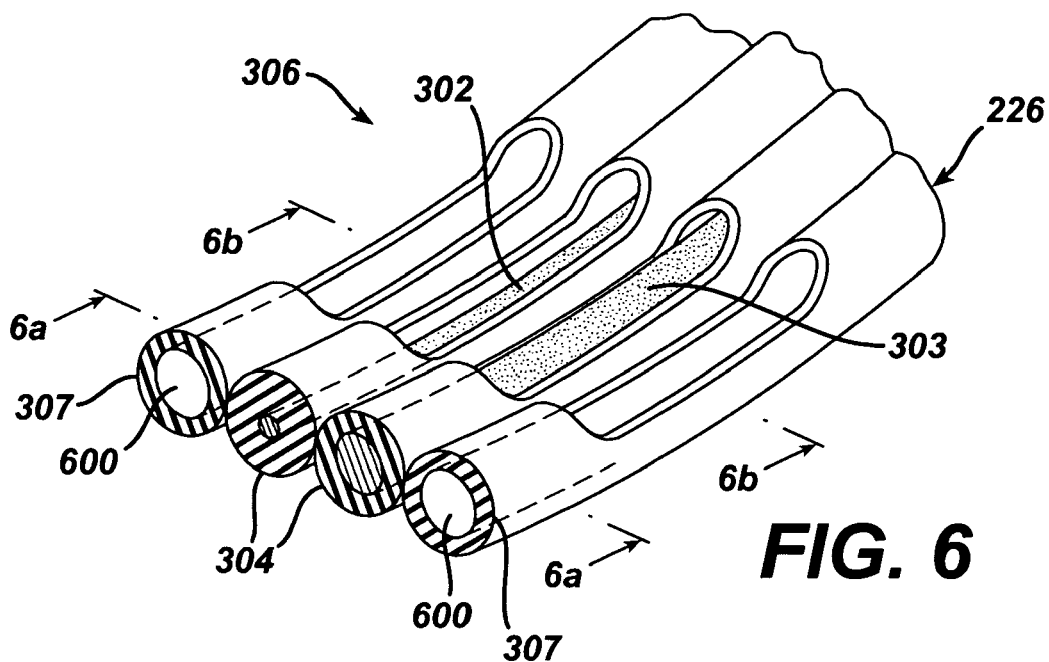
FIG. 6
FIG. 6a
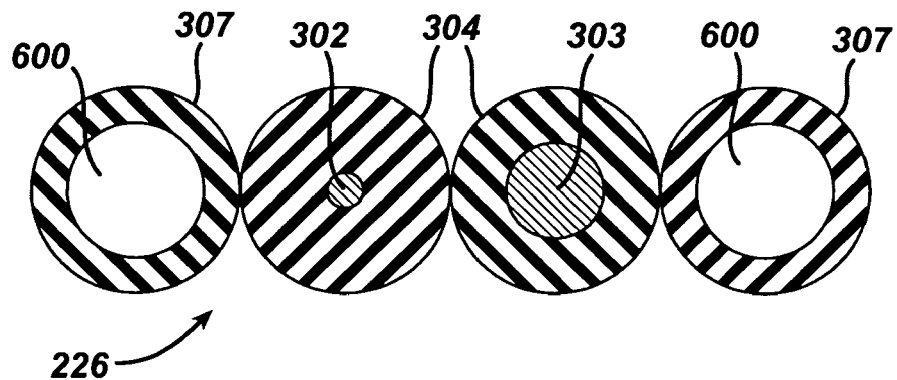
FIG. 6b
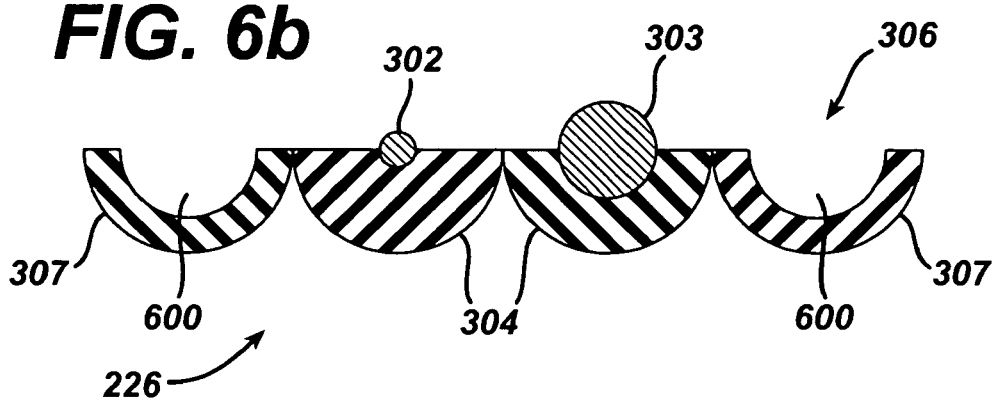

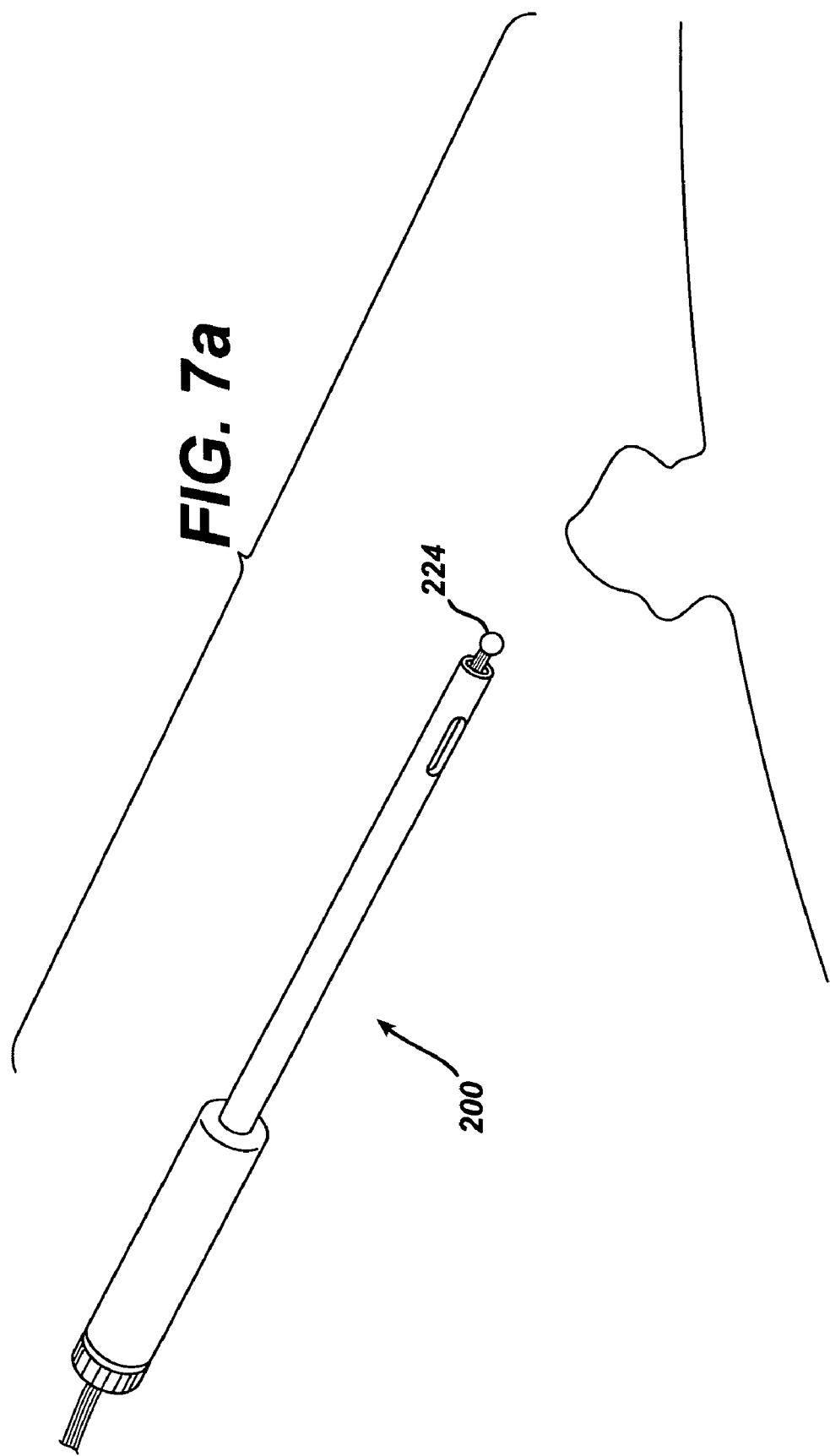

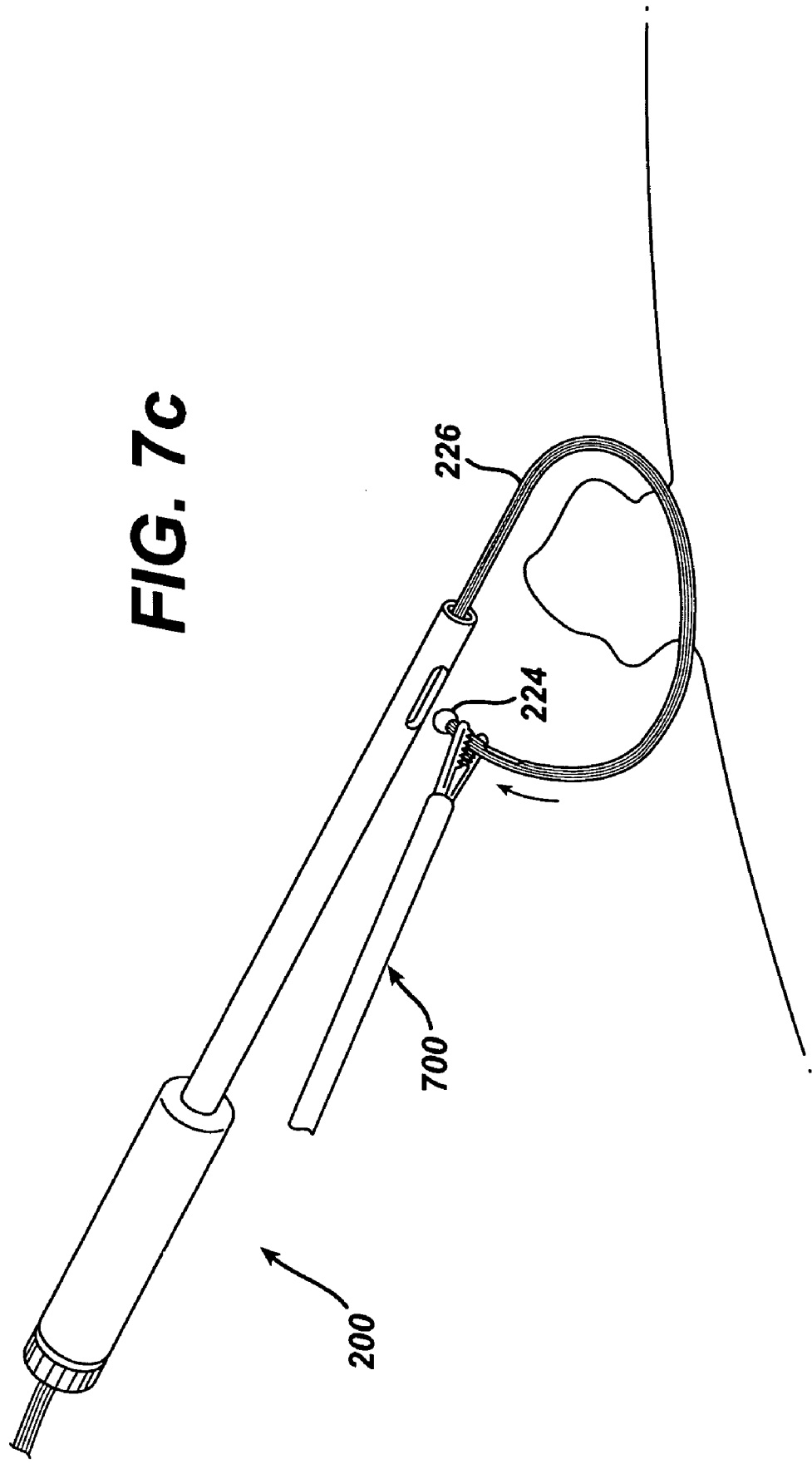

BIPOLAR ELECTROSURGICAL SNARE

FIELD OF THE INVENTION

The present invention relates to surgical instruments, and more particularly, to bipolar electrosurgical snare instruments for use in cutting and coagulating tissue.

BACKGROUND OF THE INVENTION

The utility of RF electrosurgical snares for detaching tissue structures and creating/maintaining hemostasis in both open and endoscopic surgery has been identified and addressed previously by a number of designs. U.S. Pat. Nos. 3,805,791, 3,910,279, 3,955,578, 4,202,338, and 4,345,599 describe snares that employ monopolar RF energy to cut and coagulate tissue. Although highly efficient cutting devices, the monopolar technology upon which these designs are based requires relatively high power levels and is generally associated with greater amounts of collateral tissue damage and increased risk of patient injury resulting from the inadvertent flow of current.

U.S. Pat. Nos. 3,901,242, 4,311,143, 4,493,320, 4,905,691, 5,078,716, 5,318,564, and 6,050,995 describe improved versions of the previously referenced monopolar designs which utilize bipolar RF energy to accomplish cutting. Use of bipolar instrumentation is generally associated with lower power levels, reduced amounts of collateral tissue damage and enhanced patient safety. However, conventional bipolar technology does not readily generate the current densities required for effective and rapid tissue cutting.

These known snare instruments typically consist of an insulated handle/introducer which is used to introduce the snare into the surgical site and manipulate it during use, and a section of exposed wire which can be deployed from the introducer to form a loop or lasso that captures therein the tissue to be resected. The snare instrument is introduced into the body, such as through an endoscope, with the snare in the retracted position within an introducer. When the distal end of the instrument is in close proximity to the target tissue, the snare is then fully deployed out of the end of the introducer. A grasper or other suitable device is used to grasp the end of the snare, loop it around the target tissue, and then insert it into a suitable capture mechanism on the instrument to cause the snare to form the loop referred to above. The energy source, such as a generator, is then activated while the snare is pulled toward the proximal side of the tissue to cut and cauterize the target tissue. These devices suffer from the drawbacks mentioned above.

U.S. Pat. Nos. 5,697,281, 5,697,536, 5,697,882, and 5,697,909 describe bipolar electrosurgery technology that uses a plasma pocket or bubble to provide rapid tissue vaporization or cutting with reduced collateral tissue damage as compared to monopolar electrosurgery. These patents describe a custom generator which is capable of forming and maintaining this plasma bubble in a conductive fluid media, such as normal saline, and a collection of electrodes which can be used to cut and vaporize/remove tissue. None of these prior art references or devices they disclose, however, teach or suggest the incorporation of plasma technology into an electrosurgical snare in order to overcome the deficiencies of presently existing snares as described above.

Accordingly, there is a need for an improved electrosurgical snare based on plasma technology that provides the rapid and efficient cutting commonly found only with monopolar instruments while also providing the increased safety associated with bipolar electrosurgery.

SUMMARY OF THE INVENTION

A bipolar electrosurgical instrument is provided including an introducer having a handle portion and an outer shaft coupled to the handle portion, with the introducer having a channel extending therein from an opening at a distal end of the introducer. The instrument further includes snare slidably positionable within the channel and slidable between an undeployed position wherein it is substantially retracted within the channel and a deployed position wherein a distal portion of the snare extends outwardly from the channel. At least the distal portion of the snare is insulated substantially along its length except for a predetermined exposed section. Also included is a first electrically conductive member for coupling with an RF energy source that has an active electrode exposed through the predetermined exposed section of the snare, and a second electrically conductive member for coupling with a grounding element that is positioned within the snare and has a return electrode portion exposed through the predetermined exposed section of the snare, a retention element at a distal end of the snare for securing the distal end of the snare to the introducer to thereby form a looped configuration of the snare, and at least one fluid delivery channel extending through the introducer between a fluid inlet at the proximal end of the introducer, and a fluid outlet at the distal end of the introducer that is located in proximity to the exposed section of the snare.

In one embodiment, the instrument further includes an inner shaft positioned substantially concentrically and within the outer shaft, the inner shaft having a channel extending therethrough. The snare is positionable within the inner shaft channel, and the outer and inner shafts are rotatable relative to one another.

In yet another embodiment, the outer shaft has a first aperture therein and the inner shaft has a second aperture therein. In a further embodiment, the outer and inner shafts are rotatable relative to one another to a first position wherein the first and second apertures are substantially aligned and sized and shaped to receive therein the snare retention element, and to a second position wherein the first and second apertures have a reduced overlapping area of a size and shape sufficient to allow the snare but not the snare retention element to pass therethrough. In yet another embodiment, the instrument further includes a knob that is coupled to the inner shaft for rotating the inner shaft relative to the outer shaft.

In an alternate embodiment, the at least one fluid delivery channel extends through the snare and is exposed at the predetermined exposed section of the snare. The predetermined exposed section may be on one side of the snare.

A method is also provided for electrosurgically transecting tissue. The method includes providing an electrosurgical instrument including an introducer having a handle portion and an outer shaft portion coupled to the handle portion, and having a channel extending therein from an opening at a distal end of the introducer. The instrument further has an electrically conductive snare that is couplable to an RF energy source and is slidably positionable within the channel, and a retention element at a distal end of the snare. The electrically conductive snare is substantially insulated except for at a predetermined exposed area. The method further includes, with the snare in an undeployed position wherein it is substantially retracted within the channel, positioning the introducer in the vicinity of a target tissue, slidably moving the snare from the undeployed position to a deployed position wherein a distal portion of the snare extends outwardly from the channel, securing the retention element to the introducer to thereby form a looped configuration of the snare around the target tissue, contacting the target tissue with the exposed area of the snare, and supplying an electrically conductive fluid to the vicinity of the target tissue and applying RF energy to the snare to thereby transect the target tissue.

Finally, a bipolar electrosurgical instrument is provided having an introducer having a channel therein extending from an opening at a distal end thereof, and an electrically conductive snare slidably positioned within the channel and slidable between an undeployed position wherein it is substantially retracted within the channel and a deployed position wherein a distal portion of the snare extends outwardly from the channel. The electrically conductive snare is substantially insulated, but for a predetermined exposed section, and has an active and a return electrode exposed through the exposed section. The instrument further includes a retention element at a distal end of the snare for securing the distal end of the snare to the introducer to thereby form a looped configuration of the snare, and at least one fluid delivery channel extending through the introducer between a fluid inlet and a fluid outlet at the distal end of the introducer and located in proximity to the exposed section of the snare.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIGS. 2a–2c are side views of one embodiment of an electrosurgical snare instrument according to the present invention with the snare element at various stages of deployment;

FIG. 6 is a perspective view of a portion of a snare element;

FIG. 6a is a cross-sectional view of the snare element of the embodiment of FIGS. 2a–2c;

FIG. 6b is a cross-section view of the snare element of the embodiment of FIGS. 2a–2c at the location of the window; and FIGS. 7a–7d illustrate various steps in a method for using the embodiment of FIGS. 2a–2c.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways.

Figure 1:
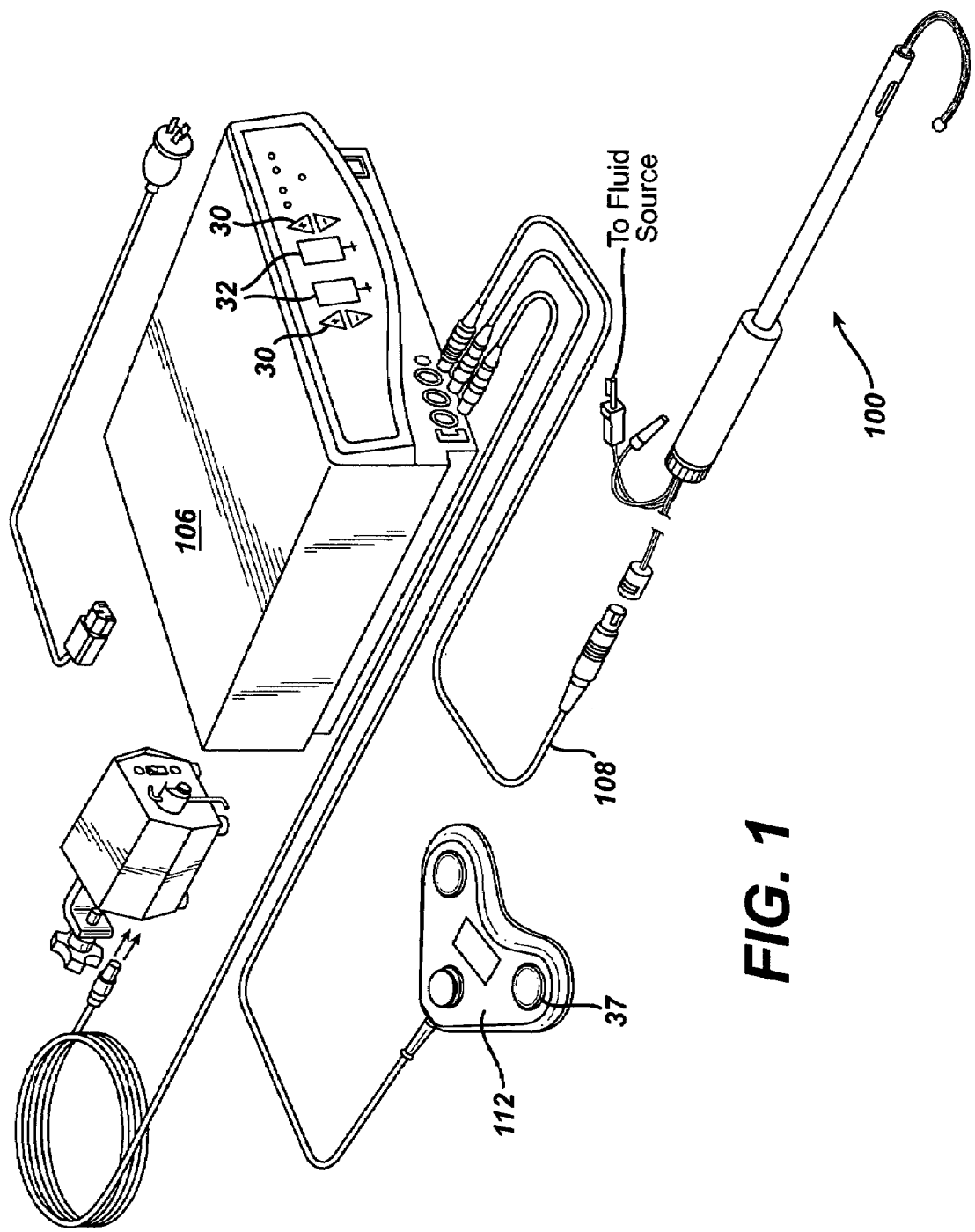
FIG. 1 illustrates a bipolar electrosurgical snare according to the present invention connected to a bipolar electrosurgical generator.

A bipolar electrosurgical snare instrument according to the present invention is shown in detail in FIGS. 1–7. FIG. 1 illustrates such a bipolar electrosurgical snare instrument 100 connected to a bipolar electrosurgical generator 106 by cable 108, and a fluid source (not shown). The bipolar generator 106 has operator controllable voltage level adjustments 30 to allow changing of the applied voltage level, which is observable at the voltage level displays 32. The generator also includes one or more foot pedals 37, which allow the surgeon to control the flow of electricity to the instrument. A suitable generator is manufactured by ArthroCare, Inc. of Sunnyvale, Calif.

Figure 2A:
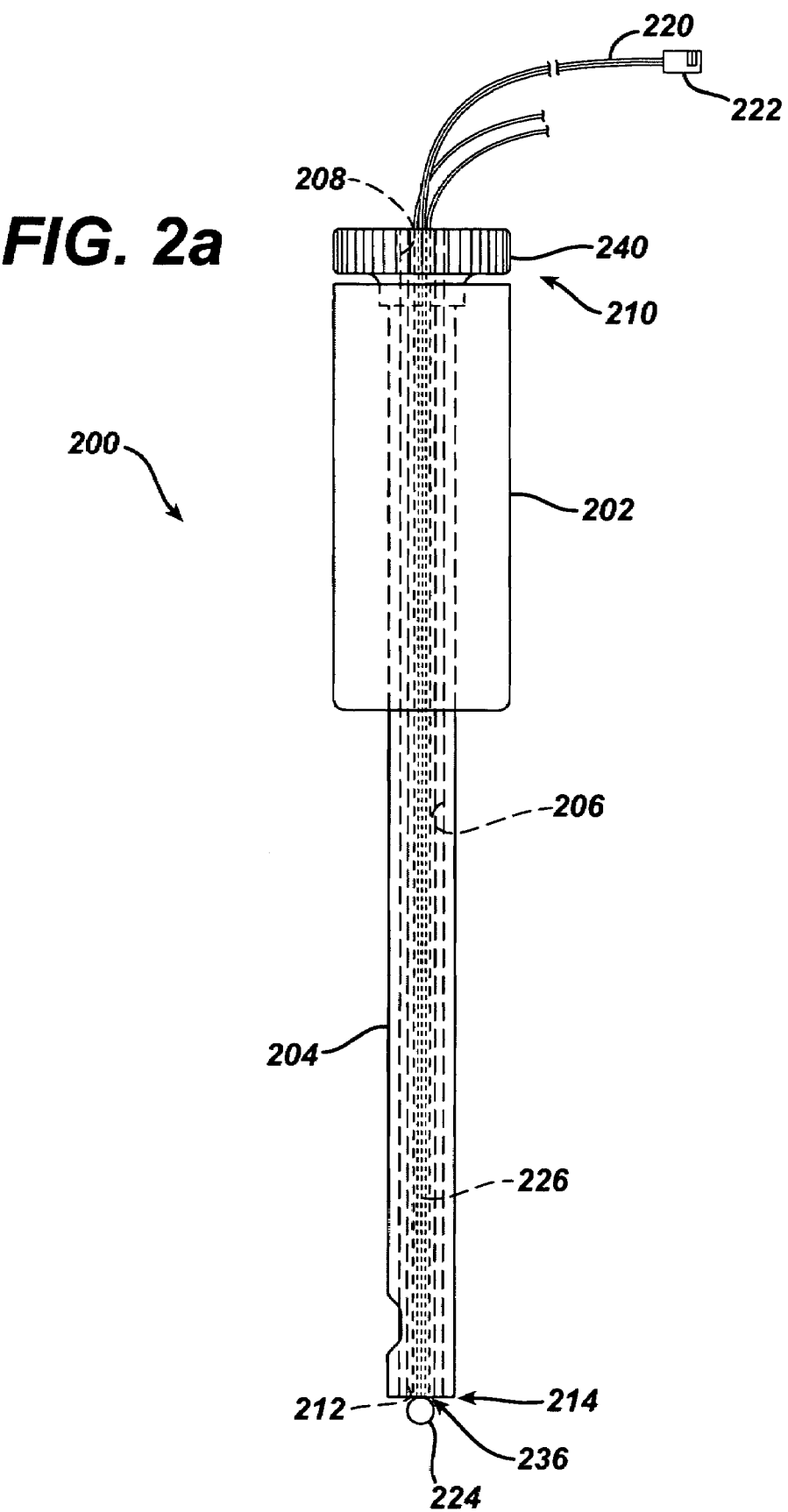
Figure 2C:
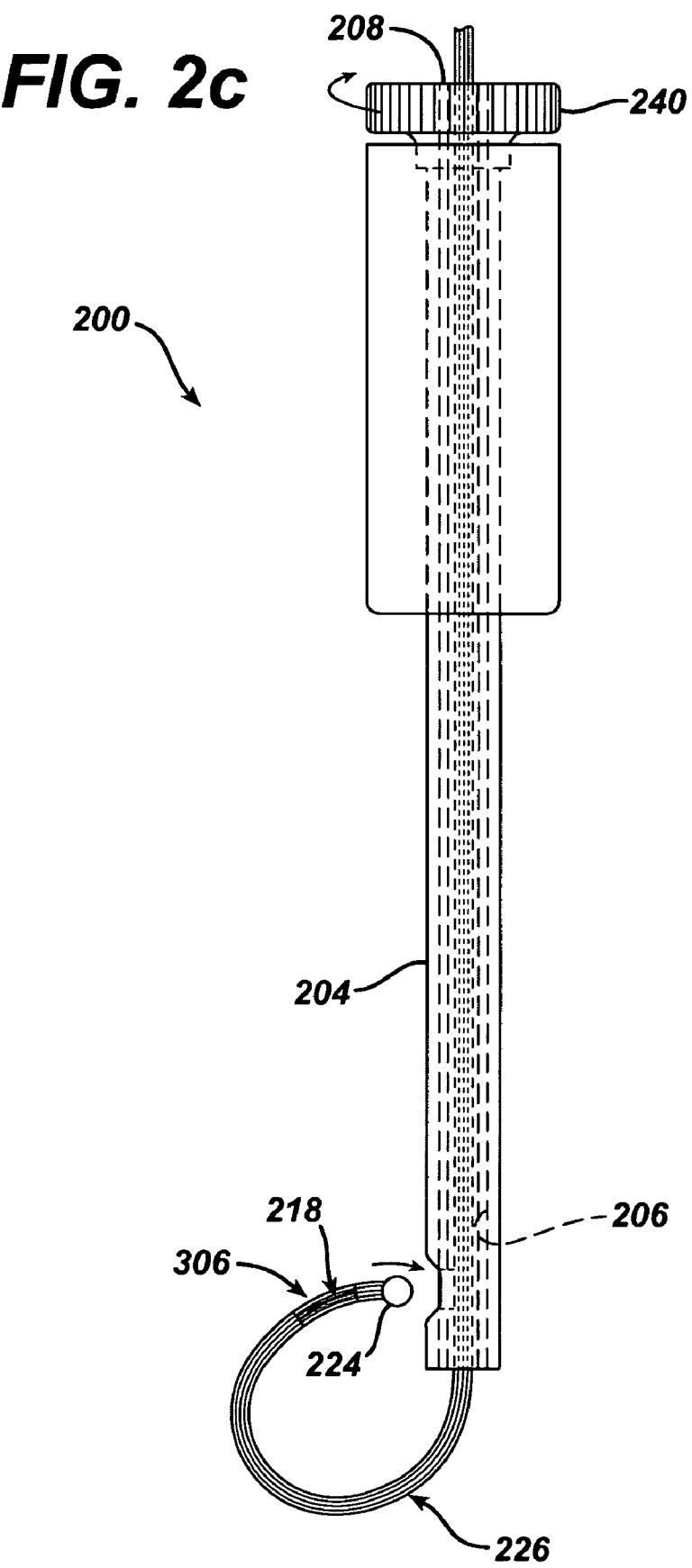

Referring now to FIGS. 2a–2c, a preferred embodiment of an electrosurgical instrument 200 according to the present invention is shown. The instrument possesses a pair of concentric hollow shafts 204, 206 and includes a handle portion 202 for grasping and manipulating the instrument. The outer shaft portion 204 extends from and is affixed to the handle portion. The inner shaft portion 206 is arranged within the outer shaft and is fixed to a rotating knob 240 or the like at the proximal end 210 of the instrument. The inner and outer shafts are sized relative to one another so that the inner shaft is rotatable within the outer shaft by manipulation of the knob 240. A channel extends through the inner shaft 206 between a first opening 208 at the proximal end 210 of the instrument and a second opening 212 at the distal end 214 of the instrument. The handle will be of any suitable, well known design and configuration to enable a surgeon to grasp and manipulate the device from an exterior of the surgical port. The handle portion 202, rotating knob 240, and inner and outer shafts may be comprised of any combination or arrangement of suitable, sufficiently rigid biocompatible material, such as plastic or stainless steel. Typically, the outer shaft should have a diameter of less than approximately 5 mm and a length of at least 35 cm so as to be able to pass through an endoscopic or other surgical port.

The instrument 200 further includes a flexible snare element 226 that is slidably positioned within the channel. The snare element is slidably movable between a first undeployed position shown in FIG. 2a, wherein the snare element is substantially positioned or retracted within the channel, and a second deployed position wherein a distal portion 218 of the snare is positioned outside of the outer shaft as shown in FIGS. 2b and 2c. FIG. 2b illustrates the snare at one point during the transition from the undeployed to deployed positions. A retention element 224 is located at the distal end of the snare element, and is used to secure the distal end of the snare to the introducer to thereby form a looped configuration of the snare in a manner that will be described in more detail below.

Figure 3:
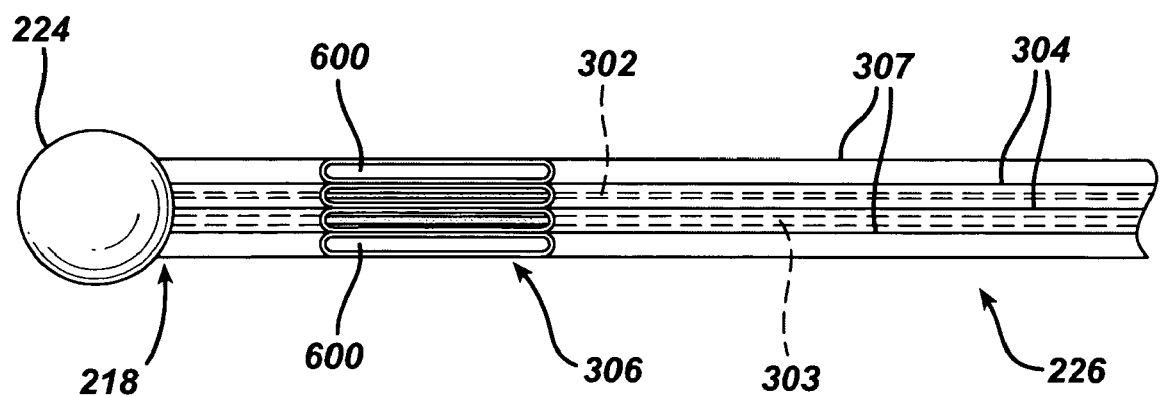
FIG. 3 is a side view of the distal end portion of the embodiment of FIGS. 2a–2c.

Preferably, as shown in FIG. 3, the snare element 226 consists of a first electrically conductive material inner member 302 that is surrounded by an insulating member 304 substantially along its entire length, but for an opening 306 in the insulating member at a predetermined location. The opening 306 exposes the electrically conductive inner member at that location. The size of the opening must be sufficient to provide a suitable cutting length, preferably on the order of 1 cm in length. The electrically conductive inner member 302 forms the active element of the bipolar pair and is electrically coupled via one or more wires through cable 220 to a source of energy, such as the bipolar generator described above. The instrument also includes a second electrically conductive member 303 that is insulated from the first electrically conductive member and from the surroundings except in the vicinity of the opening 306. This second member 303 forms the return element of the bipolar pair and is substantially larger in diameter and surface area than the first member 302 and electrically coupled via one or more wires through cable 220 to the generator. The first and second electrically conductive members must be formed of a metal that is able to resist the high current levels and heat required for plasma cutting. Suitable metals include platinum, platinum-irridium, tungsten, and molybdenum we well as numerous alloys of the same. The construction of a preferred embodiment of the snare element is described in greater detail below in conjunction with FIGS. 6–6b.

Figure 4A:
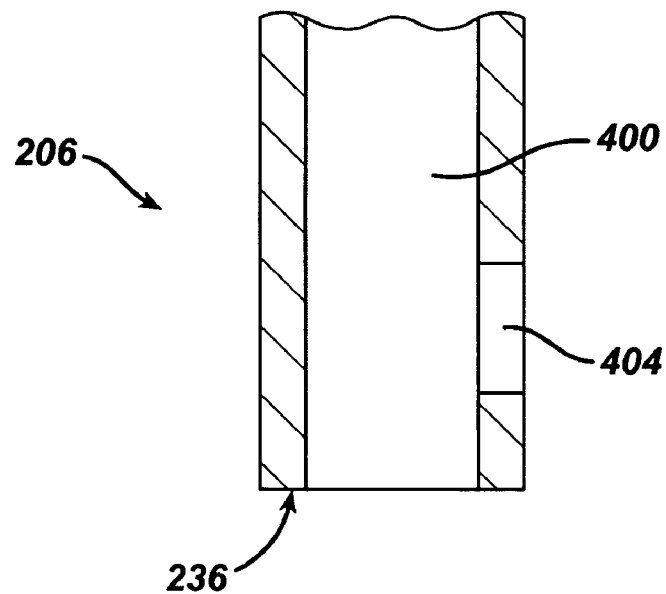
FIGS. 4a and 4b are side views of distal end portions of the inner and outer shafts of the embodiments of FIGS. 2a–2c.
Figure 4B:
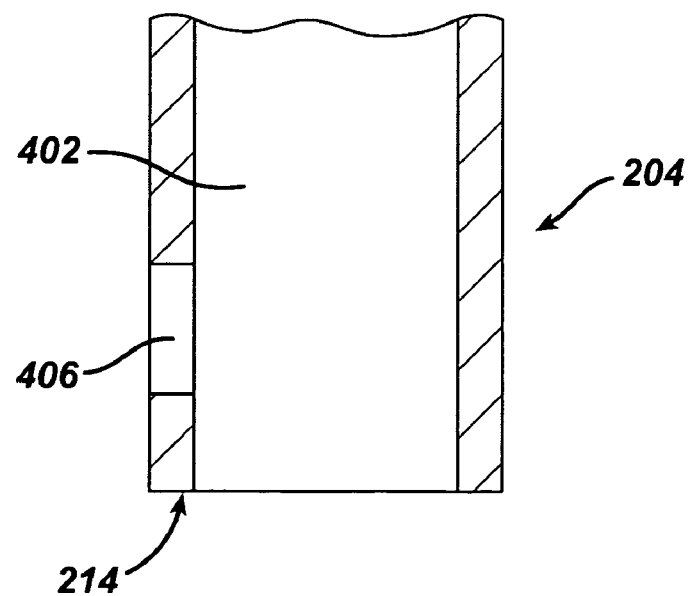
Figure 5A:
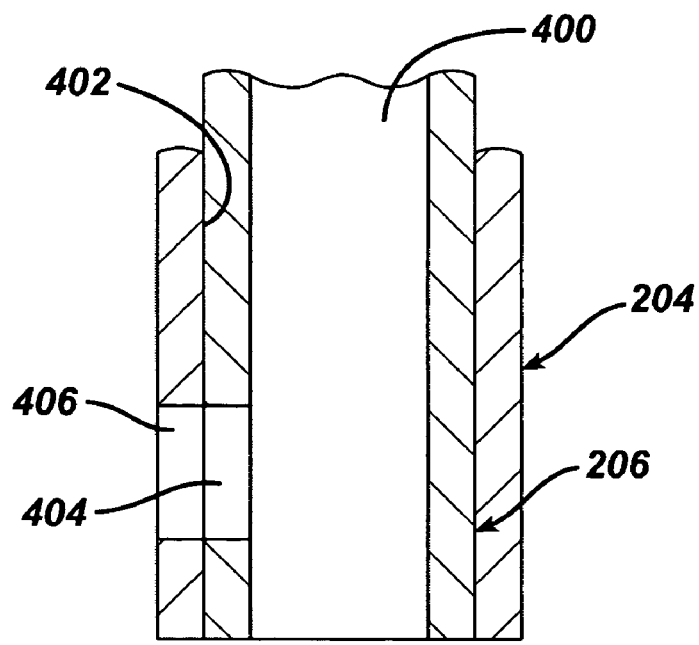
FIGS. 5a and 5b illustrate the distal end portions of FIGS. 4a and 4b together, and rotated to first and second positions relative to one another.
Figure 5B:
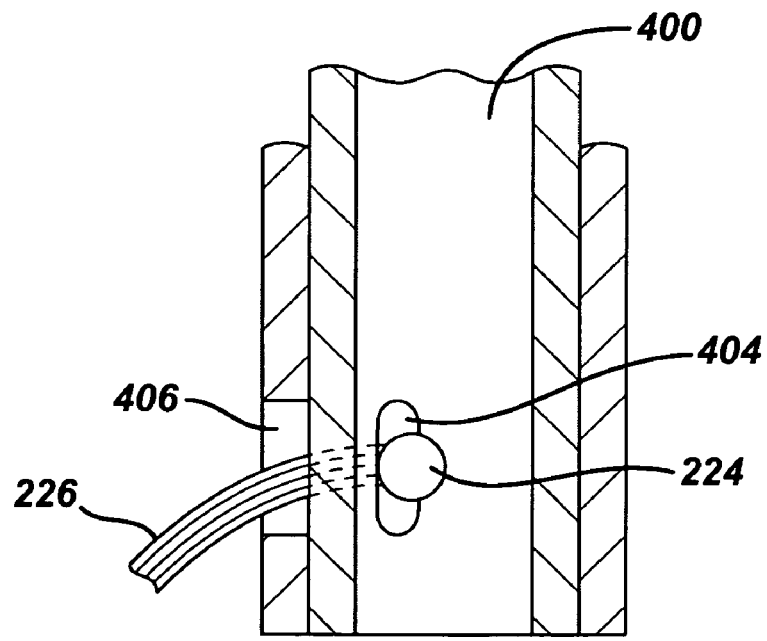

Referring now to FIGS. 4a and 4b, the distal ends 236, 214 of the inner and outer shafts respectively further have apertures 404, 406 therein. The apertures are positioned so that, when the inner and outer shafts are rotated relative to one another they can be aligned (see FIG. 5a). The apertures are further sized and shaped relative to the retention element 224 at the distal end of the snare so that when the inner and outer shafts are rotated relative to one another to a first position shown in FIG. 5a, the retention element can be inserted through the opening which is larger than the retention element. However, when the inner and outer shafts are rotated relative to one another to a second position shown in FIG. 5b, the opening becomes smaller than the size of the retention element (yet large enough to allow the snare element to pass through) so that the retention element becomes locked inside the inner shaft channel. In this manner, the retention element can be grasped or captured within the introducer, causing a looped configuration of the snare element as seen in FIG. 2c.

As is further illustrated in FIG. 2c, the inner shaft 206 is coupled to a rotating element 240 such as a knob or the like that can be grasped and manipulated by the user. Rotational movement of the rotating element causes corresponding rotating movement of the inner shaft relative to the outer shaft as described above.

Finally, the electrosurgical instrument includes one or more fluid supply conduits that supply fluid from a fluid source to an area in close proximity with the exposed portion of the snare element. In one embodiment illustrated in FIGS. 6–6b, the snare element consists of a flexible multi-lumen extrusion that incorporates the active and return electrodes 302, 303 and the one or more fluid supply conduits 600 into an integral unit. The extrusion is nominally made from silicone or any other flexible material that can withstand high temperatures without significant degradation. FIG. 6a illustrates the cross-section of the snare element substantially along its length other than in the vicinity of the opening 306, whereas FIG. 6b illustrates the cross-section at the opening 306. As can be seen, the upper portion of the insulating element 304 and of the element surrounding and forming the fluid conduits 307 (which preferably are of the same integral material), is removed to form opening 306. This exposes both the active and return electrodes, and the fluid conduits, so that fluid, when supplied, is delivered in close proximity to the active electrode to enable the plasma cutting described above. Exposing the active and return electrodes on just one side allows cutting in only one direction while preventing inadvertent damage to surrounding tissue.

Figure 7B:
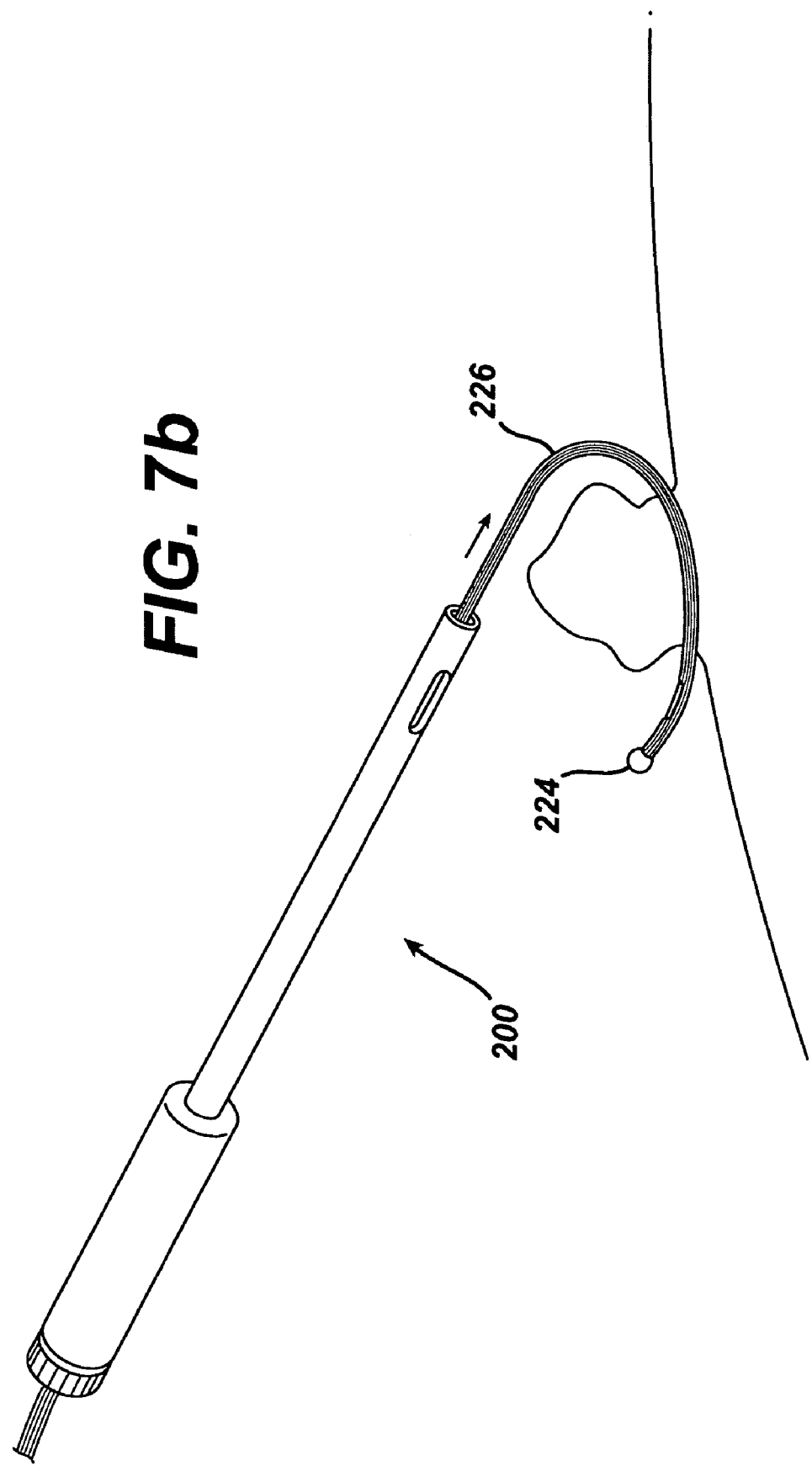
Figure 7D:
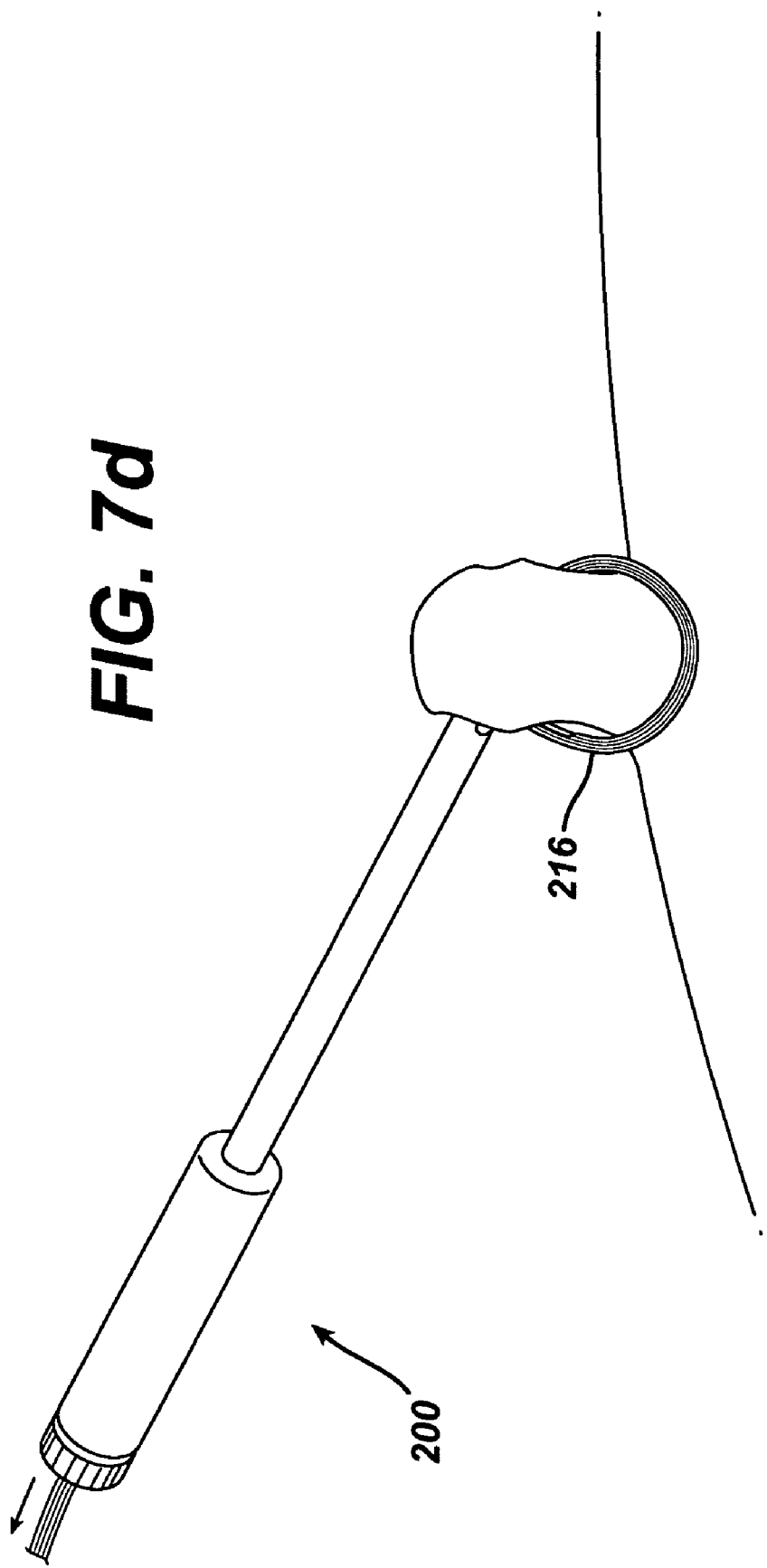

Operation of the electrosurgical instrument will now be described in greater detail with reference to FIGS. 7a–7d. FIG. 7a illustrates the distal tip of the instrument 200 as it approaches the target tissue that is to be resected. To reach the target tissue, the instrument is inserted through a trocar or surgical port in a manner well known in the art. As shown, the snare element is substantially in its fully retracted position. Once the instrument is properly positioned, a grasper 700 or other suitable instrument is used to grasp the distal end of the snare and pull the snare outward to its fully deployed position as shown in FIG. 7b. Subsequently, the grasper 700 is used (FIG. 7c) to further manipulate the distal end of the snare to insert the retention element 224 into the aperture(s) in the inner and outer shafts. The inner and outer shafts are then rotated relative to one another to maintain the retention element within the inner shaft channel as described above, resulting in a looped configuration of the snare as shown in FIG. 7d. In this manner, a loop is formed around the target tissue, with the exposed portion of the snare element (that portion that is accessible through the opening 306 shown in FIG. 3) touching or in proximity to the target tissue.

RF energy is then applied through the snare element, and fluid is delivered via the fluid delivery mechanism to the vicinity of the exposed portion of the snare element. The RF energy at the exposed portion of the snare, in combination with the fluid, will cause vaporization of the tissue that is in contact with the exposed portion of the snare. By manipulating the positioning of the distal end of the instrument, the exposed portion of the snare is manipulated relative to the target tissue until the tissue has been resected in its entirety. To remove the instrument from the body, the retention element is released from the aperture(s) by once again rotating the inner and outer shafts relative to one another, the snare element is fully retracted, and the instrument withdrawn from the body through the trocar.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A bipolar electrosurgical instrument comprising:
   an introducer having a handle portion and an outer shaft coupled to the handle portion, the introducer having a channel extending therein from an opening at a distal end of the introducer;
   a snare slidably positionable within the channel and slidable between an undeployed position wherein it is substantially retracted within the channel and a deployed position wherein a distal portion of the snare extends outwardly from the channel, wherein at least the distal portion of the snare is insulated substantially along its length except for a predetermined exposed section;
   a first electrically conductive member for coupling with a source of RF energy, the first electrically conductive member being positioned within the snare and having an active electrode exposed through the predetermined exposed section of the snare;
   a second electrically conductive member for coupling with a grounding element, the second electrically conductive member being positioned within the snare and having a return electrode portion exposed through the predetermined exposed section of the snare;
   a retention element at a distal end of the snare for securing the distal end of the snare to the introducer to thereby form a looped configuration of the snare; and
   at least one fluid delivery channel extending through the introducer between a fluid inlet at the proximal end of the introducer and a fluid outlet at the distal end of the introducer that is located in proximity to the exposed section of the snare;

wherein the active electrode has a surface area sufficiently smaller than the return electrode such that application of RF energy to the active electrode causes vaporization of fluid between the active and return electrodes, forming a plasma bubble substantially adjacent to the active electrode.

2. The instrument according to claim 1, further comprising an inner shaft positioned substantially concentrically and within the outer shaft, the inner shaft having a channel extending therethrough, and the snare being positionable within the inner shaft channel, and the outer and inner shafts being rotatable relative to one another.

3. The instrument according to claim 2, wherein the outer shaft has a first aperture therein and the inner shaft has a second aperture therein.

4. The instrument according to claim 3, wherein the outer and inner shafts are rotatable relative to one another to a first position wherein the first and second apertures are substantially aligned and sized and shaped to receive therein the snare retention element.

5. The instrument according to claim 4, wherein the outer and inner shafts are rotatable relative to one another to a second position wherein the first and second apertures have a reduced overlapping area of a size and shape sufficient to allow the snare but not the snare retention element to pass therethrough.

6. The instrument according to claim 5, further comprising a knob coupled to the inner shaft for rotating the inner shaft relative to the outer shaft.

7. The instrument according to claim 1, wherein the at least one fluid delivery channel extends through the snare and is exposed at the predetermined exposed section of the snare.

8. The instrument according to claim 1, wherein the predetermined exposed section is on one side of the snare.

9. A method for electrosurgically transecting tissue comprising:
providing an electrosurgical instrument including an introducer having a handle portion and an outer shaft portion coupled to the handle portion, and having a channel extending therein from an opening at a distal end of the introducer, and further having an electrically conductive snare that is couplable to a source of RF energy and that is slidably positionable within the channel, and a retention element at a distal end of the snare, the electrically conductive snare being substantially insulated except for at a predetermined exposed area;
with the snare in an undeployed position wherein it is substantially retracted within the channel, positioning the introducer in the vicinity of a target tissue;
slidably moving the snare from the undeployed position to a deployed position wherein a distal portion of the snare extends outwardly from the channel;
securing the retention element to the introducer to thereby form a looped configuration of the snare around the target tissue;
contacting the target tissue with the exposed area of the snare;
supplying an electrically conductive fluid to the vicinity of the target tissue and applying RF energy to the snare to thereby transaction the target tissue.

10. The method according to claim 9, wherein the electrosurgical instrument further includes at least one fluid delivery channel extending through the introducer between a fluid inlet at the proximal end of the introducer and a fluid outlet at the distal end of the introducer that is located in proximity to the exposed section of the snare.

11. The method according to claim 10, wherein the at least one fluid delivery channel extends through the snare and is exposed at the predetermined exposed section of the snare.

12. The method according to claim 9, wherein the instrument further includes an inner shaft positioned substantially concentrically and within the outer shaft, the inner shaft having a channel extending therethrough and the snare being positionable within the inner shaft channel, and the outer and inner shafts being rotatable relative to one another.

13. The method according to claim 12, wherein the inner and outer shafts further have first and second apertures therein respectively, and wherein the step of securing the retention element further comprises substantially aligning the first and second apertures, inserting the retention element into the inner shaft channel through the first and second apertures, and rotating the inner and outer shafts relative to one another to thereby secure the retention element within the inner shaft channel.

14. The method according to claim 9, further comprising, after transecting the tissue, moving the snare from the deployed position to the undeployed position, and removing the instrument from the vicinity of the target tissue.

15. A bipolar electrosurgical instrument comprising:
an introducer having a channel therein extending from an opening at a distal end thereof;
an electrically conductive snare slidably positioned within the channel and slidable between an undeployed position wherein it is substantially retracted within the channel and a deployed position wherein a distal portion of the snare extends outwardly from the channel, the electrically conductive snare being substantially insulated but for a predetermined exposed section, and having an active and a return electrode exposed through said exposed section;
a retention element at a distal end of the snare for securing the distal end of the snare to the introducer to thereby form a looped configuration of the snare; and
at least one fluid delivery channel extending through the introducer between a fluid inlet and a fluid outlet at the distal end of the introducer and located in proximity to the exposed section of the snare;
wherein the active electrode has a surface area sufficiently smaller than the return electrode such that, application of RF energy to the active electrode causes vaporization of fluid between the active and return electrodes, forming a plasma bubble substantially adjacent to the active electrode.

16. The instrument according to claim 15, wherein the introducer further includes a handle portion and an outer shaft adjacent to and extending from the handle portion.

17. The instrument according to claim 16, further comprising an inner shaft positioned substantially concentrically and within the outer shaft, wherein the snare is slidably positioned within the inner shaft.

18. The instrument according to claim 17, wherein the inner and outer shafts have first and second apertures therein respectively, and wherein the inner and outer shafts are rotatable relative to one another to a first position wherein the first and second apertures are substantially aligned, and a second position wherein the first and second apertures are not substantially aligned.

19. The instrument according to claim 18, wherein, when the inner and outer shafts are in the first position, the retention element is insertable through the first and second apertures into an interior of the inner shaft, and wherein when the inner and outer shafts are in the second position, the retention element is not insertable into the interior of the inner shaft.

20. The instrument according to claim 15, wherein the at least one fluid delivery channel extends through the snare and is exposed at the predetermined exposed section of the snare.

* * * * *